United States Patent [19]

Shea

[11] Patent Number: 4,813,941
[45] Date of Patent: Mar. 21, 1989

[54] PNEUMOTHORAX TREATMENT DEVICE

[76] Inventor: Leslie Shea, P.O. Box 490, Sagle, Id. 83860

[21] Appl. No.: 92,778

[22] Filed: Sep. 3, 1987

[51] Int. Cl.$^4$ ............................................. A61M 5/00
[52] U.S. Cl. .................................. 604/247; 604/177; 604/272
[58] Field of Search ............... 604/247, 222, 411, 414, 604/264, 272, 177; 137/854, 858

[56] References Cited

U.S. PATENT DOCUMENTS

| | | | |
|---|---|---|---|
| 2,867,213 | 1/1959 | Thomas, Jr. | |
| 3,758,073 | 9/1973 | Schulte | |
| 3,788,327 | 1/1974 | Donowitz et al. | |
| 4,244,378 | 1/1981 | Brignola | |
| 4,244,379 | 1/1981 | Smith | |
| 4,354,492 | 10/1982 | McPhee | 604/247 |
| 4,366,817 | 1/1983 | Thomas | 604/174 |
| 4,465,062 | 8/1984 | Versaggi et al. | |
| 4,468,224 | 8/1984 | Enzmann et al. | 604/247 |
| 4,556,086 | 12/1985 | Raines | 604/247 |
| 4,683,916 | 8/1987 | Raines | 604/247 |

Primary Examiner—Stephen C. Pellegrino
Attorney, Agent, or Firm—Wells, St. John & Roberts

[57] ABSTRACT

An apparatus is disclosed for providing immediate temporary treatment of pneumothorax in a patient by exhausting the pleural cavity. The apparatus incorporates an exhaustion device having a standard luer lock lug receptacle enabling use of a multiple of different size and models of pleural cavity entrance devices having standard luer lock connecting lugs. The exhaustion device also incorporates a one-way valve on the luer lock lug receptacle for exhausting fluid from the pleural cavity and preventing fluid from flowing into the pleural cavity. Projecting wings ease the handling of the apparatus and provide tape attachment surfaces for securing of the apparatus to a patient.

13 Claims, 2 Drawing Sheets

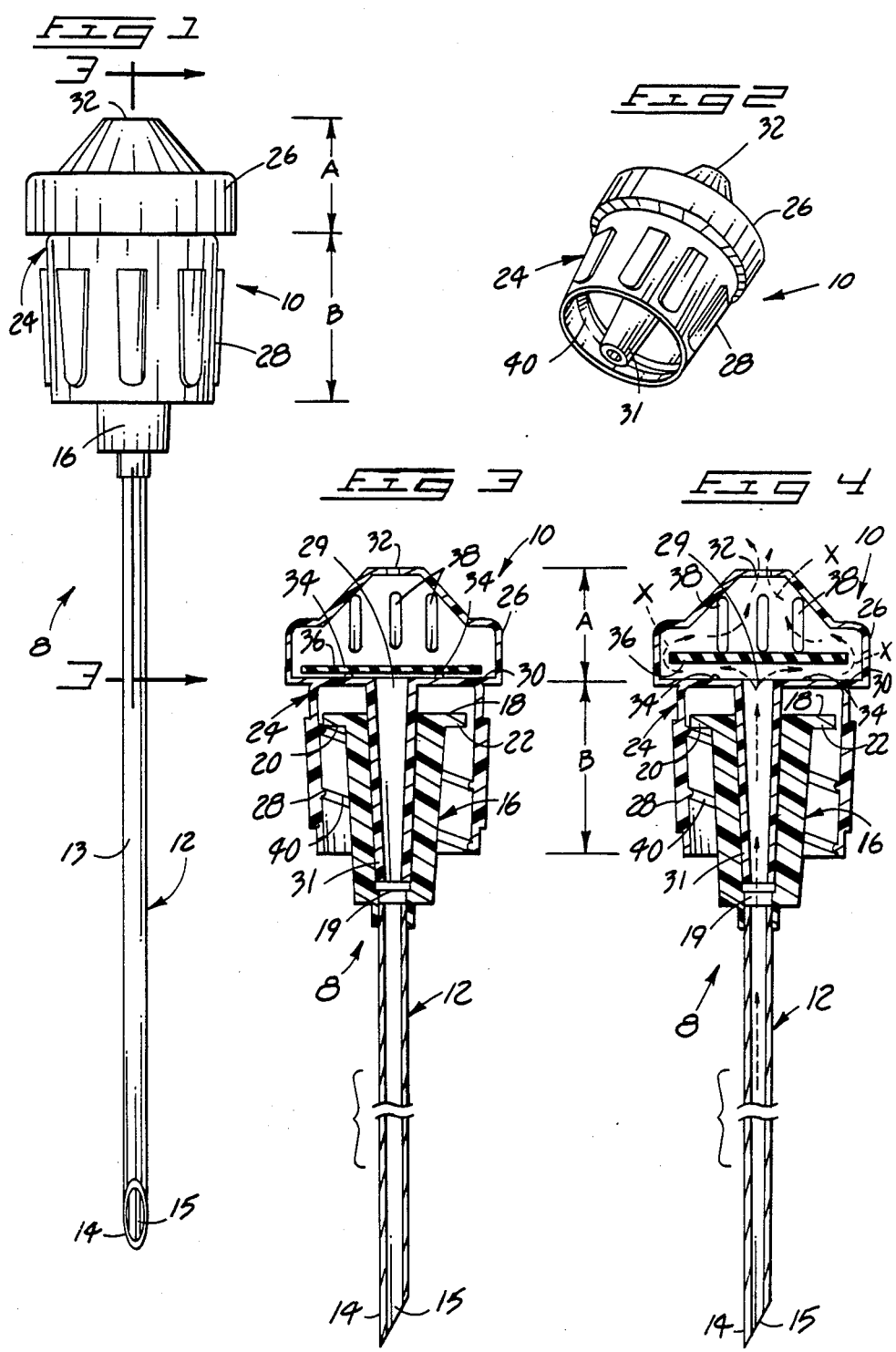

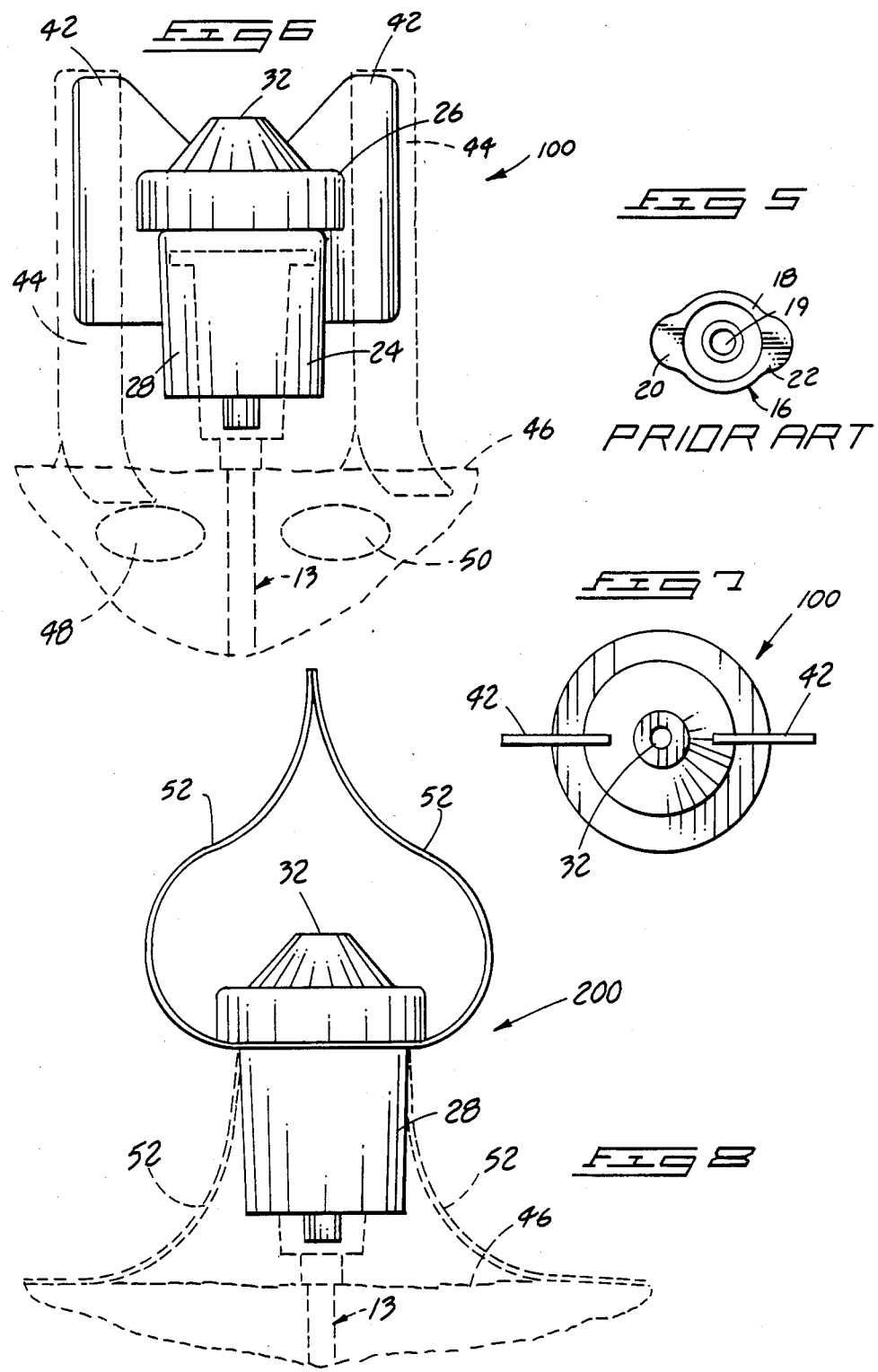

PNEUMOTHORAX TREATMENT DEVICE

TECHNICAL FIELD

This invention relates to devices and methods for treating pneumothorax.

BACKGROUND OF THE INVENTION

The thorax or chest cavity of a person contains the lungs and mediastinum which holds the heart and major vessels. The lungs are retained within a pair of airtight pleural cavities within the thorax. Respiration occurs as the result of a partial vacuum being maintained within each of these pleural cavities.

When we breathe in, our muscles cause the chest walls to move out and our diaphragm at the lower portion of the thorax to move down. This increases the volume of the thorax and pleural cavities, resulting in a corresponding pressure drop. The lungs, being exposed to greater atmospheric pressure through airways to the mouth or nose, expand with air to fill the increasing volume and equalize the pressure difference. When a person breathes out, the chest walls move in and the diaphragm moves up which squeezes the lungs and forces air from the lungs through the airways.

The lungs have no muscles or other control of their own to keep them in an expanded condition. The only means of lung expansion is the partial vacuum which is created when the chest wall moves out and the diaphragm moves down. If the partial vacuum is released or not able to be maintained, there is nothing to expand the lung, and it collapses. Pneumothorax is the condition where air or other gas is present in at least one of the pleural cavities which prevents expansion of a lung. It occurs spontaneously as a result of disease, injury or lung tissue, or puncture of the chest wall. If the partial vacuum is not restored to the pleural cavities, pneumothorax can be fatal.

A number of methods and devices are available for treating pneumothorax. One method requires the making of an incision between a pair of ribs and inserting a chest tube into the affected pleural cavity. The tube is then connected to a vacuum source for evacuating the cavity to enable the patient to breathe while the cause and ultimate treatment for the pneumothorax are determined. Another method employs the insertion of a needle into the affected pleural cavity and connecting the needle by a long tube to a one-way valve device which enables exhausting of air from the pleural cavity and prevents air from re-entering the pleural cavity. Yet another method employs use of a conventional hypodermic syringe for aspirating air from a pleural cavity using the syringe plunger.

These and other present accepted methods are not without drawbacks. For example, it can be difficult and time consuming to properly insert the chest tube. Specialized equipment is not always readily available and, when available, requires extreme care in use. Additionally, most current products require different sized apparatuses for use on different size patients. Further, most of the specialized products are costly.

A need remains for an improved device for providing immediate temporary treatment of pneumothorax.

BRIEF DESCRIPTION OF THE DRAWINGS

Preferred embodiments of the invention are illustrated in the accompanying drawings, in which:

FIG. 1 is a side elevational view of an apparatus in accordance with the invention for providing immediate temporary treatment of pneumothorax;

FIG. 2 is a perspective view of an exhaustion device in accordance with the invention;

FIG. 3 is a cross-sectional fragmentary view of the apparatus taken along line 3—3 in FIG. 1;

FIG. 4 is a cross-sectional fragmentary view similar to FIG. 3 showing a one-way valve means component of the apparatus exhausting fluid through the apparatus;

FIG. 5 is a top end view of a conventional luer lock lug;

FIG. 6 is a side elevational view of an alternate embodiment exhaustion device in accordance with the invention;

FIG. 7 is a top view of the exhaustion device of FIG. 6; and

FIG. 8 is a side view of another alternate embodiment exhaustion device in accordance with the invention.

DETAILED DESCRIPTION OF THE PREFERRED EMBODIMENT

The following disclosure of the invention is submitted in compliance with the constitutional purpose of the Patent Laws "to promote the progress of science and useful arts" (Article 1, Section 8).

A first embodiment apparatus in accordance with the invention is indicated in the figures generally by reference numeral 8. Apparatus 8 is comprised of an exhaustion device 10 and a pleural cavity entrance device 12. Such a combination is capable of providing immediate treatment of pneumothorax in a patient by exhausting the affected pleural cavity. The apparatus is intended primarily to provide temporary relief until a surgical procedure can be performed to secure a more permanent solution and investigate the cause of the pneumothorax.

Pleural cavity entrance device 12 is illustrated in the form of a conventional hypodermic needle 13 having an elongated shaft and an angled end 14 which provides a sharp point for penetrating through the skin and into the affected pleural cavity. Needle 13 is generally hollow having a passageway 15 extending therethrough for transferring fluid, primarily air or other trapped gas, from the pleural cavity. The end of needle 13 opposite pointed end 14 is connected to a luer lock connector lug 16. Luer lock connecting lug 16 is also conventional and includes an end flange portion 18 having radially opposed projections 20, 22. A passageway 19 is formed through the center of luer lock lug 16. Passageway 19 is in communication with passageway 15 of needle 13 for transmitting fluid through the end of luer lock lug 16.

Alternate pleural cavity entrance devices could be employed without departing from the principles and scope of the invention. For example, a trocar and flexible cannula could be used which enables removal of the trocar after pentrating the pleural cavity. However, all such pleural cavity entrance devices usable in accordance with the invention necessarily require a luer lock lug 16 as will be more fully described below.

Exhaustion device 10 of apparatus 8 comprises a one-piece outer housing 24. Housing 24 is longitudinally elongated having a first or top end section A and a second or bottom end section B. Section A comprises a one-way valve means 26 for exhausting fluid from the pleural cavity and preventing fluid from flowing into the pleural cavity. Section B comprises luer lock lug receiving means 28 which is sized and configured for threadably receiving luer lock lug 16 on pleural cavity entrance device 12. A laterally or radially extending separation wall 30 separates one-way valve means 26 from luer lock lug receptacle 28. Wall 30 includes a central opening or hole 29. A hollow tubular projection 31 extends from about opening 29 of lateral wall 30 and through the center of luer lock lug receptacle 28 to provide fluid communication between one-way valve means 26 and luer lock lug receptacle 28.

One-way valve mean 26 is generally hollow including an exhaust opening 32 at its top or outermost longitudinal end. An annular valve seat or rib 34 projects longitudinally from lateral wall 30 in the direction of exhaust opening 32 and encircles opening 29. A flexible circular diaphragm 36 bears against valve seat 34 and extends radially outward beyond the valve seat. A plurality of diaphragm stops 38 extends inward into the hollow portion of one-way valve means 26 from housing 24 from adjacent exhaust opening 32 towrad diaphragm 36. These function to prevent diaphragm 36 from being outwardly forced against exhaust opening 32 by pressure within hollow tube 31.

Luer lock lug receiving means 28 is also generally hollow having internal threads 40 which are sized and configured for threadably receiving luer lock connecting lug 16 on pleural cavity entrance device 12. Luer lock lug 16 thrheads into the luer lock lug receptacle 28 such that tube 31 extends into lug passageway 19. A fluid tight seal is thereby formed therebetween.

Pressure within hollow tube 31 will cause diaphragm 36 to be displaced from valve seat 34 in the direction of exhaust opening 32. This will enable fluid, primarily air, to flow around diaphragm 36 as indicated by dashed lines "X" (FIG. 4). However, greater pressure on the exhaust opening side of diaphragm 36 than within hollow tube 31 forces diaphragm 36 against valve seat 34. This effectively covers and seals opening 29 preventing fluid from flowing through exhaust opening 32 and subsequently through the hypodermic needle. Accordingly, fluid is able to flow from housing 24 in only one direction outwardly through exhaust opening 32.

The structural features of exhaustion device 10 provide the significant advantages of being usable with readily available syringes and trocars which have the substantially universal luer lock lugs 16 thereon. The combination of a one-way valve means and luer lock lug receptacle in a compact housing enables rapid connection of the exhaustion device to various sized needles or other pleural cavity entrance devices that are used for different sized patients.

FIG. 6 illustrates an alternate embodiment apparatus 100 which includes wing means in the form of a pair of radially opposed wings 42 which project from housing 24. As shown, wings 42 project from the longitudinal positions of both one-way valve means 26 and luer lock lug receiving means 28. Wings 42 also longitudinally extend beyond exhaust opening 32 to prevent accidental taping of such exhaust opening. Wings 42 provide at least one of two functions. First, they provide an enlarged portion for grasping by a user of the exhaustion device for ease of attachment to a pleural cavity entrance device. Second, they provide tape attachment surfaces for taping the apparatus to the patient after connection to the pleural cavity entrance device which has been inserted into the patient. FIG. 6 illustrates pieces of tape 44 being draped over each of wings 42 and extending to the patient's skin 46 for securing exhaustion device 100 thereto. Hypodermic needle 13 is shown extending through the patient's skin 46 and between a pair of ribs 48, 50.

FIG. 8 illustrates yet another embodiment apparatus 200 having tape or other adhesive strips 52 attached to the housing 24 during manufacture. Such strips can include removable backing pieces (not shown) for preserving the adhesive until exposure for use. Strips 52 are illustrated as being secured to each other above exhaust opening 32 providing finger-holds to facilitate installation of apparatus 200 to the pleural cavity entrance device. The adhesive strips are used by pressing them to the patient's skin 46 as shown in phantom.

The exhaustion devices can be used in at least two ways. Preferably, a pleural cavity entrance device such as a syringe with a hypodermic needle is first inserted into a patient's pleural cavity for immediate exhaustion of trapped fluid. Shortly thereafter, the syringe is removed with the needle remaining in place. This enables the bulk of the trapped air within the pleural cavity to be exhausted. The exhaustion device is then threaded to the luer lock lug on the hypoderic needle to provide an effective seal and the desired functioning of the one-way valve. This enables the remainder of the trapped air to be exhausted for restoring the necessary partial wacuum to the affected pleural cavity. Alternately and less preferable the exhaustion device can be threaded to the luer lock lug on the pleural cavity entrance device prior to insertion into the patient's pleural cavity.

Exhaustion devices constructed in accordance with the invention enable immediate temporary treatment of pneumothorax using existing readily available pleural cavity entrance devices which have the universal luer lock lug connector thereon. The exhaustion devices are inexpensive, easily stored and readily adapted for use by emergency vehicle crews.

In compliance with the statute, the invention has been described in language more or less specific as to structural features. It is to be understood, however, that the invention is not limited to the specific features shown, since the means and construction herein disclosed comprise preferred forms of putting the invention into effect. The invention is, therefore, claimed in any of its forms or modifications within the proper scope of the appended claims, appropriately interpreted in accordance with the doctrine of equivalents.

I claim:

1. An apparatus for connection to a pleural cavity entrance device having a luer lock lug thereon to provide immediate temporary treatment of pneumothorax in a patient by exhausting the pleural cavity, comprising:

a housing having a top end and a bottom end;

one-way valve means on the housing between the top and bottom ends for receiving fluid through the bottom housing end from the pleural cavity and exhausting the fluid through the top housing end while preventing fluid from flowing back through the housing and into the pleural cavity;

luer lock lug receiving means on the bottom end of the housing, the luer lock lug receiving means including a threaded portion sized and configured for threadably receiving the luer lock lug on the pleural cavity entrance device, the luer lock lug receiving means being in fluid communication with the one-way valve means through the housing for exhausting fluid from the pleural cavity through the pleural cavity entrance device and one-way valve means, and means having enlarged surfaces which project from the housing providing an enlarged portion for grasping by a user of the apparatus and for providing tape attachment surfaces for receiving tape for taping the apparatus to the patient.

2. The apparatus of claim 1 wherein the housing is elongated between the top and bottom ends, and wherein the one-way valve means and luer lock lug receiving means are longitudinally spaced relative to one another.

3. The apparatus of claim 2 wherein the wing means laterally projects from exterior surfaces of the housing from the longitudinal positions of both the one-way valve means and the luer lock lug receiving means.

4. The apparatus of claim 3 wherein the one-way valve means includes an exhaust opening, the wing means longitudinally projecting relative to the exhaust opening to prevent accidental taping of the exhaust opening.

5. The apparatus of claim 2 wherein the wing means longitudinally extends as well as laterally projects relative to the housing.

6. The apparatus of claim 2 wherein the one-way valve means includes an exhaust opening, the tape attachment surfaces being spaced outwardly relative to the exhaust opening a sufficient distance to prevent accidental taping of the exhaust opening.

7. The apparatus of claim 1 further comprising adhesive strips connected to the housing for securing the apparatus to the patient.

8. An apparatus for providing immediate temporary treatment of pneumothorax in a patient by exhausting the pleural cavity, comprising:
 pleural cavity entrance means for penetrating the pleural cavity from the exterior of the patient, the pleural cavity entrance means including a passageway for exhaustion of fluid from the pleural cavity therethrough, and further including a luer lock connecting lug;
 luer lock lug receptacle means having a threaded portion sized and configured for threadably receiving the luer lock connecting lug on the pleural cavity entrance means; and
 one-way valve means on the luer lock lug receptacle means, the one-way valve means having a bottom end connected to the luer lock receptacle means, said bottom end being in fluid communication with the passageway of the pleural cavity entrance means for receiving fluid therefrom, and a top end for exhausting fluid from the pleural cavity and means between the top and bottom ends for preventing fluid from flowing back through the passageway into the pleural cavity.

9. The apparatus of claim 8 further comprising wing means which project outwardly from the luer lock lug receptacle and one-way valve means for providing an enlarged portion for grasping by a user of the apparatus, and for providing tape attachment surfaces for taping the apparatus to the patient.

10. The apparatus of claim 9 wherein the luer lock lug receptacle means and one-way valve means are longitudinally oriented relative to one another, the wing means longitudinally and laterally extending relative to the one-way valve means.

11. The apparatus of claim 9 wherein the one-way valve means includes an exhaust opening, the tape attachment surfaces being spaced outwardly relative to the exhaust opening a sufficient distance to prevent accidental taping of the exhaust opening.

12. The apparatus of claim 9 wherein the one-way valve means includes an exhaust opening, the wing means longitudinally projecting relative to the exhaust opening to prevent accidental taping of the exhaust opening.

13. The apparatus of claim 8 further comprising adhesive strips connected to the apparatus for securing the apparatus to the patient.

* * * * *